US006517847B2

(12) United States Patent
Dow et al.

(10) Patent No.: US 6,517,847 B2
(45) Date of Patent: *Feb. 11, 2003

(54) TOPICAL GEL DELIVERY SYSTEM

(75) Inventors: Gordon J. Dow, Santa Rosa, CA (US); Robert W. Lathrop, Novato, CA (US); Debra A. Dow, Petaluma, CA (US)

(73) Assignee: Dow Pharmaceutical Sciences, Petaluma, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/096,516

(22) Filed: Mar. 8, 2002

(65) Prior Publication Data

US 2002/0176891 A1 Nov. 28, 2002

Related U.S. Application Data

(63) Continuation of application No. 09/632,508, filed on Aug. 3, 2000, now Pat. No. 6,387,383.

(51) Int. Cl.[7] .......................... A61K 7/00; A61K 47/00
(52) U.S. Cl. .................... 424/401; 424/404; 424/78.02; 424/78.03; 424/78.06; 514/772; 514/859; 514/563; 514/886; 514/871; 514/887
(58) Field of Search ................................ 424/401, 404, 424/78.02, 78.03, 78.06; 514/772, 859, 863, 886, 871, 887

(56) References Cited

U.S. PATENT DOCUMENTS

| | | |
|---|---|---|
| 4,247,547 A | 1/1981 | Marks |
| 4,361,584 A | 11/1982 | Fulton, Jr. |
| 4,387,107 A | 6/1983 | Klein et al. |
| 4,497,794 A | 2/1985 | Klein et al. |
| 4,514,385 A | 4/1985 | Damani et al. |
| 4,671,956 A | 6/1987 | Bouillon et al. |
| 4,692,329 A | 9/1987 | Klein et al. |
| 4,906,617 A | 3/1990 | Jacquet et al. |
| 4,933,177 A | 6/1990 | Grollier et al. |
| 5,380,528 A | 1/1995 | Alban et al. |
| 5,382,432 A | 1/1995 | McCook et al. |
| 5,446,028 A | 8/1995 | Klein et al. |
| 5,451,405 A | 9/1995 | Zhang et al. |
| 5,466,446 A | 11/1995 | Steifel et al. |
| 5,538,732 A | 7/1996 | Smith et al. |
| 5,614,201 A | 3/1997 | Slavtcheff et al. |
| 5,690,923 A | 11/1997 | DeVringer et al. |
| 5,721,275 A | 2/1998 | Bazzano |
| 5,733,558 A | 3/1998 | Breton et al. |
| 5,750,122 A | 5/1998 | Evans et al. |
| 5,767,098 A | 6/1998 | Klein et al. |
| 5,891,451 A | 4/1999 | Guerrero et al. |
| 5,932,228 A | 8/1999 | Hall et al. |
| 6,106,848 A | 8/2000 | Preuilh et al. |
| 6,387,383 B1 * | 5/2002 | Dow et al. .................. 424/401 |

FOREIGN PATENT DOCUMENTS

| | | |
|---|---|---|
| EP | 0 479 518 A1 | 4/1992 |
| WO | WO 90/14833 | 12/1990 |

OTHER PUBLICATIONS

Product Guide. Carbopol: The Proven Polymers in Pharmaceuticals, Bulletin 2, pp. 1–2, Copyright 1994 The B.F. Goodrich Co.

* cited by examiner

Primary Examiner—Thurman K. Page
Assistant Examiner—Rachel M. Bennett
(74) Attorney, Agent, or Firm—Cooley Godward LLP; Tom M. Moran

(57) ABSTRACT

A composition is provided that has a viscosity of less than about 15,000 cP and a pH of about 3.0 to 9.0 for treating a skin disorder in a human subject. The composition is a lotion that consists essentially of (a) a therapeutically-effective amount of at least one compound useful for treating such disorder, (b) a pharmaceutically-acceptable, lightly cross-linked polyacrylic acid polymer compatible with the compound, (c) a pharmaceutically acceptable base to adjust pH, (d) up to about 25% ww of at least one water miscible solvent, (e) optionally a preservative, (f) water, and (g) an oil phase component and suitable surfactant. The composition is useful for treating an inflammatory skin disorder, acne, or rosacea.

31 Claims, No Drawings

TOPICAL GEL DELIVERY SYSTEM

CROSS-REFERENCE

This application is a continuation application of application Ser. No. 09/632,508, filed Aug. 3, 2000, now U.S. Pat. No. 6,387,383, the entire content of which is hereby incorporated by reference.

BACKGROUND OF THE INVENTION

1. Field of Invention

This invention relates to a composition for treating a skin disorder in a human, and a method of administering and preparing such composition.

2. Background

Skin disorders are a common problem in childhood, adolescence and adulthood. Skin disorders can include, for example, acne, inflammatory diseases such as atopic eczema, or rosacea.

Acne vulgaris is a follicular disease characterized by pilosebaceous inflammations such as comedones, papules, pustules, cysts and nodules. Chiefly a disease of adolescence (and often a cause of emotional distress), acne originates endogenously and stems for multifactorial influences. Major progressive factors in the development acne include hyperkeratosis of the follicular epithelium, increased sebum production, and proliferation of *Propionibacterium acnes*. These factors are primarily responsible for hyperkeratosis of the follicle lining, including retention of keratin and sebum, as well as the free fatty acid by-products of *P.acnes* metabolization which can lead to inflamed acne papules and pustules.

Although acne may also be influenced by exogeneous and hormonal factors., research has been centered around eliminating *P.acnes*, the most common cause of inflammation. To date the pathogenesis of acne is not fully understood, and there is currently no cure for the disease. Many systemic and topical medications, such as tetracycline, have been used to manage and control acne. None, however, is universally successful.

Acne treatment is typified by "polypharmacy", whereby physicians employee simultaneous treatment with a variety of modalities. The search for improved acne treatments has been widespread and continuous during the past several decades. Enhanced cosmetic properties to encourage user compliance, the use of topical therapies in place of systemic drugs to reduce toxicity and side effects, and the introduction of new drugs and formulations represent the forefront of acne treatment advances.

The first use of a topical antibiotic, erythromycin, for the treatment of acne was reported by Fulton (Fulton, J. E. Jr. and Pablo, G. *Topical antibacterial therapy for acne*. Study of the family of erythomycins. Arch. Dermatol. 110:83–86, 1974). Topical administration of these potent agents has the advantage of reduced side effects, particularly those caused by systemic drug effects, e.g., nausea, gastrointestinal upset, diarrhea, and vaginal yeast overgrowth.

Lincomycin antibiotics have been employed in the topical treatment of acne (U.S. Pat. No. 3,969,516). Lincomycin was commercialized by Upjohn Co. (now Pharmacia & Upjohn) as Cleocin T Solution, Gel, Lotion and Pledgets. Cleocin T Gel was an improvement over Cleocin T Solution because of the elimination of alcohol and the ease of application to the facial skin for the treatment of acne. This gel is based on carbomer 934, NF.

Atopic dermatitis is a polygenic disease with an inherited predelection and strongly influenced by environmental factors. The condition affects infants, children, adolescents and adults and is allergic in nature. The distribution is symmetrical, typically involving the face, neck and flexural areas. Atopic dermatitis is chronic, relapsing and usually pruritic. Topical treatment frequently includes topical corticosteroids, such as desonide, hydrocortisone valerate, fluocinolone acetonide, triamcinolone acetonide, betamethasone valerate, hydrocortisone butyrate, halobetasol propionate, betamethasone dipropionate, clobetasol propionate, difloransone diacetate, fluticasone propionate, budesonide or the like.

Rosacca is a chronic inflammatory eruption of the nose, face and other flushing areas of the skin. The disease is most common in middle aged women and is characterized by erythema, papules, pustules, telangiectasia and enlarged sebaceous glands. The cause etiology is not totally clear; however vasomotor lability and menopause are predisposing factors. The organism Demodex folliculorum is found frequently in the contents of inflamed pustular follicles, and has a possible role in this skin disorder. Treatments include topical metronidazole and oral tetracycline type antibiotics.

SUMMARY OF THE INVENTION

One aspect of this invention is a composition having a pH of about 3.0 to about 9.0 and a viscosity of less than about 15,000 centipoise (cP) for treating a skin disorder in a human subject. The composition comprises (a) a therapeutically-effective amount of at least one compound useful for treating such disorder, (b) a pharnaceutically-acceptable polyacrylic acid polymer compatible with the compound, (c) optionally a water miscible solvent, (d) optionally a preservative, (e) optionally an oil phase and surfactant, and (f) water.

Another aspect of the invention is a composition described above in combination with a container that accurately administers a portion of the composition for topical administration to a patient.

Another aspect of the invention is a composition described above in combination with labeling instructions for use in treating the skin disorder.

Still another aspect of the invention is a method for treating a skin disorder in a human subject, which method comprises administering a composition described above to an affected area of the subject's skin having such disorder in an amount and for a period of time sufficient to improve the skin disorder.

Still another aspect of the invention is a method for preparing a composition of this invention by combining water with a therapeutically-effective amount of a suitable compound and the polymer and optionally a water-miscible solvent and preservative. If a lotion is desired an oil phase is formed for integration with the aqueous phase.

Other aspects of the invention may be apparent upon further reading the specification and claims of the patent application.

SPECIFIC DESCRIPTION

This invention provides a novel topical gel or lotion delivery system for the treatment of skin diseases, particularly acne vulgaris. One unique aspect of the system is the use of a polymeric material that provides a gel material that has a very low viscosity but which is cosmetically elegant and aids in the administration process by providing a pourable composition that flows through a dropper tip easily.

The Composition

One aspect of this invention is a composition having a pH of about 3 to about 9 and a viscosity of less than about 15,000 cP for treating a skin disorder in a human subject. The composition comprises a therapeutically-effective amount of at least one compound useful for treating such disorder, a pharmaceutically-acceptable, lightly cross-linked polyacrylic acid polymer compatible with the therapeutically-effective compound, optionally a water miscible solvent, optionally a preservative, and water. The composition may include a solution of the active compound or a suspension. A lotion will also include a pharmaceutically-acceptable oil phase emulsified with one or more surfactants.

The composition is useful to treat skin disorders, e.g. acne, rosacea, or inflammatory skin diseases such as atopic dermatitis. The composition will include an active agent that will be one compound alone or two or more compounds in combination. The active agent can be an antibiotic, a corticosteroid, a retinoid, an anti-inflammatory imidazole, a non-steroidal anti-inflammatory agent (NSAID), or a combination.

An antibiotic is generally viewed as a drug that inhibits the growth of an unwanted microorganism. Representative examples of topical antibiotics include lincomycins, (e.g. clindamycin), erythromycin, minocycline, and tetracycline, and the pharmaceutically-acceptable salts, esters, or pro-drugs thereof. Preferred is clindamycin phosphate.

A "retinoid" is a keratolytic drug related to retinoic acid and generally includes chemical entities such as retinol and its esters and closely related naturally-occurring derivatives and structurally-related synthetic analogs. This includes, for example, retinol, retinal, tretinoin (all-trans retinoic acid), isotretinoin, adapalene (6-[3-(1-adamantyl)-4-methoxyphenyl]-2-naphthoic acid), and the like. Of these, tretinoin is preferred.

Generally, a topical corticosteroid is a compound that is a structural modification of hydrocortisone (also known as cortisol) and that shows topical anti-inflammatory activity. Representative examples include those set forth in Table 65-1 at page 1575 of "Goodman & Gilman's The Pharmacological Basis of Therapeutics," Eighth Edition, McGraw-Hill, Inc. (1993). Specific, non-limiting examples of topical cortiocosteroids include those mentioned in the "background" section of this application. Preferred corticosteroids, when used as a single active agent, include diflorasone diactetate, fluticasone propionate, halobetasol propionate, or budesonide. Halobetasol propionate is most preferred when used as a single active ingredient.

Nonsteroidal anti-inflammatory agents (NSAIDs) are compounds that suppress the inflammatory response when topically applied by inhibiting prostaglandin synthesis or by other mechanisms of action. Examples may be found in Goodman and Gilman, Ibid. Representative examples include ibuprofen, indomethacin, diclofenac, and naproxen and their salts. Preferred is diclofenac.

An anti-inflammatory imidazole is an imidazole compound that suppresses a topical inflammatory response. Metronidazole is a representative imidazole compound suitable for this invention.

In describing the details of the composition, the numerical ranges given herein are those amounts that provide the functional results in the composition. Thus, the ranges are generally introduced with the term "about" to indicate a certain flexibility in the range, i.e. ±10% or less at the lower and upper numerical ranges given.

As mentioned, the active agent may be present alone or in combination. For example, a topical antibiotic, such as clindamycin phosphate, may be combined with a topical corticosteroid. Where a formulation is designed primarily for application to the facial area, to treat acne for example, it is preferred to combine an antibiotic (e.g. clindamycin phosphate) with a less potent corticosteroid, such as desonide, hydrocortisone valerate, fluocinolone acetonide, hydrocortisone butyrate, or triamcinolone acetonide. The topical antibiotic can also be combined with a retinoid, e.g. clindamycin phosphate and tretinoin or adapalene.

The composition of the invention will include a polymeric material that will be present in an amount sufficient to bring the viscosity of the composition to a level of not more than about 15,000 cP, preferably between about 100 and about 12,000, and more preferably between about 300 and about 10,000. The viscosity is determined at room temperature (20–25° C.) using a Brookfield viscometer model DV-I+, spindle #27 at 12 revolutions per minute (rpm). If the measured viscosity is less than 4,000 cP, spindle #21 should be used instead of #27. By keeping the viscosity below about 15,000 cP, the advantages of more appealing cosmetic characteristics and ease of accurate application through improved flow and pourability are achieved.

The polymers that have been found to be particularly useful in the composition of the present invention are lightly cross-linked polyacrylic acid polymers which are available from B.F. Goodrich under the tradename CARBOPOL®. They are generically referred to as carbomers. The CARBOPOL polymers are hydrophilic polymers based on a polyacrylic acid structure. For use in the present invention the lightly cross-linked polymers include CARBOPOL 910, 941, 971, and 981 and CARBOPOL ETD 2050.

Either CARBOPOL 941 or 981 is particularly valuable for the present invention because the viscosity of a gel based on CARBOPOL 941 or 981 is low relative to its concentration. This feature is the result of the low level of cross-linking within the polymer structure in a neutralized aqueous system. In contrast polyacrylic acid polymers which display a high level of cross-linking, such as CARBOPOL 980 or 974P, produce gels with higher viscosity at comparable concentrations.

A 0.5% solution of either CARBOPOL 941 or 981 at pH 7.5 has a viscosity measurement of from 4,000 to 11,000 cP (Brookfield viscometer at 20 rpm) compared to a viscosity measurement of from 40,000 to 60,000 cP for a comparable 0.5% solution of either CARBOPOL 940 or 980 (reference: B.F. Goodrich Product Guide, Bulletin 2).

This lower-level viscosity feature of the lightly cross-linked polyacrylic acid polymers, e.g. CARBOPOL 941 and 981, offers two advantages to the composition of the present invention. A gel made from one of these lightly cross-linked polymers provides better skin feel and lubricity than a gel of comparable viscosity made from a highly cross-linked polymer. Second, a low viscosity gel can be administered very accurately by a dropper or drip-type dispenser as compared to other commercial products which are thicker gels that do not provide as accurate an application.

CARBOPOL 941 NF resin and its cosolvent polymerized alternative, CARBOPOL 981 NF resin, provide permanent emulsions and suspensions at low viscosities. The gels produced with these resins have excellent clarity. In ionic systems, they perform better than most of the other CARBOPOL resins and at concentrations below 1.5% in solvent systems. The polymers are available from B.F. Goodrich Specialty Chemicals, 9911 Brecksville Road, Cleveland, Ohio 44414-3247.

CARBOPOL resins are polymers of acrylic acid crosslinked with polyalkenyl ethers or divinyl glycol. The polymers are flocculated powders of primary particles averaging about 0.2 micron in diameter. The flocculated powders are agglomerates that average 2 to 7 microns as determined by Coulter Counter. These agglomerates cannot be broken down into the primary particle once produced.

Each primary particle can be viewed as a network structure of polymer chains interconnected by crosslinks. Without the crosslinks, the primary particle would be a collection of linear polymer chains intertwined but not chemically bonded. These linear polymers are soluble in a polar solvent, such as water. They swell in water up to 1000 times their original volume (and ten times their original diameter) to form a gel, especially when exposed to a pH environment above about 4–6. Since the $pK_a$ of these polymers is 6.0±0.5, the carboxylate groups on the polymer backbone ionize, resulting in repulsion between the negative particles, which adds to the swelling of the polymer. Highly crosslinked polymers of this type do not dissolve in water, rather they form gels by forming homogeneous dispersions.

The glass transition temperature of CARBOPOL resin is 105° C. (221° F.) in powder form. However, the glass transition temperature drops dramatically as the resin comes into contact with water. The polymer chains start gyrating and the radius of gyration becomes bigger and bigger. Macroscopically, this phenomenon manifests itself as swelling.

The aqueous composition of the invention, will optionally include a water miscible solvent and a preservative. The water miscible solvent (i.e. a cosolvent) will be present if needed, to assist in dissolving the active agent. The cosolvent may be a single component or a mixture. Examples include those that are miscible with water such as ethanol, propylene glycol, glycerin, polyethylene glycol 400, and the like. Certain water-miscible solvents, such as glycerin or propylene glycol, also add beneficial humectant properties to the composition. Drug delivery and penetration into the skin can be modified by the water-miscible cosolvent composition.

The preservative useful in the composition is material that aids in ensuring a stable composition and/or prevents growth of bacteria. Thus, a preservative may be one or more of an antioxidant, a chelator, an antibacterial, or the like. Suitable preservatives include methylparaben, butylparaben, propylparaben, benzyl alcohol, sorbic acid, imidurea, thimerisal, propyl gallate, BHA, BHT, citric acid, disodium edetate, and the like. Another optional additive is a fragrance. Generally, this will be present in a trace amount only and has no effect on the functioning of the composition.

A preferred composition, particularly for the treatment of acne, will exhibit a pH of about 3 to 9, preferably about 4 to 7, and most preferably at about 5 to 6. Thus, the composition may also include a pH-adjusting agent as needed at a level to adjust the pH to the desired range. Such agents include many pharmaceutically-acceptable organic or inorganic bases, e.g., sodium hydroxide and tromethamine. The pH chosen will depend in part on the pH tolerance of the active agent chosen for the composition. The examples provide guidance for certain compounds and suitable pH values for the compositions.

Another aspect of this invention is an emollient embodiment, i.e., a fluid emulsion or lotion. This aspect of this invention is a composition having an internal oil phase dispersed with the aid of at least one surfactant, e.g., an emulsifier, in water. Suitable surfactants are well known in the art and include those referred to as anionic and nonionic agents. These are described in Remington: The Science and Practice of Pharmacy, Nineteenth Edition, Vol. 1 at p. 251. Representative surfactants include polysorbate 20, polysorbate 40, polysorbate 60, polysorbate 80, sorbitan laurate, sorbitan oleate, sorbitan stearate, polyoxyethylene stearate, sodium laureth sulfate, and laureth-10. Oil phase components include those that are commonly used in the art such as mineral oil, petrolatum, stearyl alcohol, cetyl alcohol, isopropyl myristate, diisopropyl adipate, stearic acid, white wax, and the like.

The following Table sets forth operational and preferred ranges of the various components for a gel composition having an active ingredient, which may be a single compound or a combination of two or more compounds. The term surfactant means one or more surfactants, which includes wetting agents and emulsifiers.

TABLE A

| | % w/w | | |
|---|---|---|---|
| Component | Operational | Preferred | More Preferred |
| Active ingredient | 0.005–10.0 | 0.01–5.0 | 0.05–2.0 |
| Polyacrylic Polymer Acid | 0.05–3.0 | 0.05–1.0 | 0.1–0.5 |
| Cosolvent | 0.0–70.0 | 0.0–40.0 | 0.0–25.0 |
| Preservative | 0.0–3.0 | 0.01–1.0 | 0.05–0.25 |
| Surfactant* | 0.0–8.0 | 0.0–5.0 | 0.0–3.5 |
| Oil phase* | 0.0–50.0 | 0.0–25.0 | 0.0–15.0 |
| Water | QSAD 100 | QSAD 100 | QSAD 100 |
| Base | QS pH | QS pH | QS pH |

*Present for lotion

The following Table B sets forth the operational, preferred, and more preferred concentrations of representative active ingredients that can beneficially be used in practicing our invention, whether alone or in combination. The exact amount will be readily determined by one of ordinary skill by referencing standard texts such as the Physicians Desk Reference or Goodman and Gilmann's referred to hereinbefore.

TABLE B

| | % w/w | | |
|---|---|---|---|
| Component | Operational | Preferred | More Preferred |
| Antibiotic | 0.1–5.0 | 0.5–2.0 | 0.5–1.0 |
| Corticosteroid | 0.005–2.5 | 0.01–1.0 | 0.05–0.1 |
| Retinoid | 0.005–0.5 | 0.05–0.1 | 0.025–0.05 |
| Imidazole | 0.1–5.0 | 0.5–2.0 | 0.75–1.0 |
| NSAID | 0.1–3.0 | 0.2–2.0 | 0.2–1.0 |

To make an emulsion (i.e., lotion) form of our invention as broadly set forth in Table A, the surfactant and oil phase component are included in the composition. The following table illustrates the manner in which the composition is modified to form a lotion.

TABLE C

| | % w/w | | |
|---|---|---|---|
| Component | Operational | Preferred | More Preferred |
| Surfactant | 0.1–8.0 | 0.5–5.0 | 1.0–3.5 |
| Oil phase | 1.0–50.0 | 2.5–25.0 | 5.0–15.0 |

The preferred formula of the composition would either be preservative-free or have a decreased level of preservatives as compared to material that is commercially available. This is important because the presence of preservatives in a composition can result in irritation or allergic reaction of the skin. Reducing the possibility of skin irritation or allergic reaction in a composition provides a better product. Regarding compositions that contain clindamycin phosphate, the leading product is Cleocin T Gel. It is a clear viscous gel that tests have shown is not as well accepted as the less viscous material of the invention made with a more lightly cross-linked polymer. By controlling the viscosity of the gel at a low level it can be accurately dispensed from a clear plastic squeeze bottle rather than from an ointment tube. The advantage is two-fold. One is accurate dosage control by using a reduced orifice tip and improved product presentation for marketing. In addition, tests have shown that the less viscous material is cosmetically more elegant and will result more regular use.

In preparing a composition of this invention general formulation techniques known in the art of pharmaceutical science will be used. See, for example, Remington: The Science and Practice of Pharmacy, Nineteenth Edition, Mack Publishing Company (1995). Preparation of specific formulations may be found in the examples.

To prepare a gel with two active ingredients where one is suspended and the other is dissolved, first add the insoluble active to a water-miscible ingredient, or a portion of the water with a surfactant, to disperse. Separately, dissolve the other active and any other preservative ingredients in the purified water. Disperse the gelling agent in the aqueous solution with appropriate stirring. Then add the dispersion of the first active ingredient to the gel and mix well to blend. Last, add a pH adjusting agent to adjust the pH to the desired range. The preparation of a gel when both active ingredients are dissolved is similar, varying only in the first step. First, add the active with lower aqueous solubility to a solvent, blend of solvents, or water. Mix to dissolve. Separately, dissolve the other active and any preservative ingredients in the purified water. Disperse the gelling agent in the aqueous solution with appropriate stirring. Then add the solution of the first active to the gel and mix well to blend. Last, add a neutralizing agent to adjust the pH to the desired range.

For a combination of an antibiotic e.g. clindamycin phosphate with a retinoid, such as tretinoin, three formulation approaches can be applied to a composition of the invention: 1) an aqueous gel, formed from a lightly crosslinked carbomer gelling agent, with the clindamycin phosphate dissolved and the tretinoin suspended; 2) an oil-in-water emulsion with the clindamycin phosphate dissolved in the water thickened with a lightly cross-linked carbomer gelling agent and the tretinoin dissolved in an internal liquid oil phase; and 3) a solution consisting of water and water-miscible organic solvents with the clindamycin phosphate and tretinoin both dissolved.

The following compositions are given as representative as the types of compositions useful in this invention.

Where the composition contains an antibiotic alone, for example clyndamycin phosphate, the composition has a pH of about 4 to 7 and contains (a) about 0.5% to 2.0% w/w clindamycin phosphate,
(b) about 0.1% to 0.4% w/w of the polymer,
(c) the base to adjust pH,
(d) about 15.0% to 25.0% w/w of a water miscible solvent,
(e) less than about 0.2% w/w of a preservative, and
(g) QSAD purified water to 100% w/w.

Preferably such a composition has a pH of about 5 to 6 and contains (a) 1.0 to 1.5% w/w clindamycin phosphate,
(b) 0.2% w/w of the polymer,
(c) the base to adjust pH,
(d) 15.0% w/w propylene glycol and 5.0% w/w polyethylene glycol 400,
(e) 0.1–0.15% w/w methylparaben, and
(g) QSAD purified water to 100% w/w.

A gel composition where the antibiotic in clindamycin phosphate and the retinoid is tretinoin may contain (a) (i) about 0.5% to about 2.0% w/w clyndanycin phosphate, and
(ii) about 0.01% to about 0;05% w/w tretinoin;
(b) about 0.1% to about 0.5% w/w of the polymer;
(c) the base to adjust pH;
(d) about 10% to about 30% w/w of a water-miscible solvent;
(e) less than about 0.2% of a preservative; and
(g) QSAD purified water 100% w/w.

A lotion composition of clindamycin phosphate and tretinoin usefully will contain (a) (i) about 0.5% to about 2.0% w/w clyndanycin phosphate and
(ii) about 0.01% to about 0.05% w/w tretinoin;
(b) about 0.1% to about 0.5% w/w of the polymer;
(c) the base to adjust pH;
(d) about 5% to about 30% w/w of a water-miscible solvent;
(e) less than about 0.2% of a preservative;
(f) an oil phase in combination with at least one surfactant to form an emulsion; and
(g) QSAD purified water 100% w/w.

Treatment

Another aspect of the invention is a method for treating a skin disorder in a human, which method comprises administering a composition to an affected area of the subject's skin having such disorder in an amount and for a period of time sufficient to improve the skin disorder, wherein the composition is described in this patent application. Preferably, the composition is administered once a day over the treatment period. Depending on the patient's improvement, the treatment may extend for less than a week to two months or more. The progress of improvement may be monitored by the patient or by a physician.

The skin disorders which are treatable with the composition of the invention include acne vulgaris, rosacea, and various inflammatory conditions including atopic dermatitis. A discussion of these conditions may be found in the Merck Manual. For example, acne vulgaris is an inflammatory disease affecting hair follicles and sebaceous glands. Lesions are most common on the face, but the neck, chest, upper back, and shoulders may also be affected.

The affected area of the subject's skin can be anywhere on the body in which the skin disorder exists. The amount of composition and period of administration time sufficient to improve the skin disorder will be dependent on the subject and skin condition. Generally, a sufficient amount will be squeezed from a dropper tip of a squeeze bottle or an eye dropper onto the area affected and rubbed gently into the skin. Usually, no more than a few drops will be needed to apply to an affected area.

Article of Manufacture

Another aspect of the invention is an article of manufacture that comprises a composition for treating a skin disorder as described above in a suitable container, preferably in a dropper bottle, in combination with labeling instructions. The dropper bottle can be made of any material, for example, glass, rigid plastic, or flexible plastic. Other means of administration are an eyedropper, or tube with a suitable small orifice size, such as an extended tip tube.

The composition of this invention may be, for example, filled and packaged into a plastic squeeze bottle (i.e., 42 g). A suitable container-closure system for the package presentation for the composition described in Table D.

TABLE D

| Nominal Size | Overflow Capacity | Material Description | Manufacturer |
|---|---|---|---|
| 1 oz | 46 cc | Natural cylinder, round polypropylene bottle, 15/415 finish, Wheaton B-21411 White low density polyethylene 15 mm dropper tip plug, Wheaton B-11048 White polypropylene extended tip closure, Wheaton B-15044 | Wheaton Plastic Products 1101 Wheaton Avenue Milville, NJ 08332 |

The labeling instructions can come in the form of a pamphlet, a label applied to or associated with the packaging of the article of manufacture.

The labeling instructions provide for administering a composition of the invention to an affected area of a subject's skin having a skin disorder, in an amount and for a period of time sufficient to improve the skin disorder. Printed labeling instructions are functionally related to the composition of the invention inasmuch as such labeling instructions describe a method to treat a skin disorder. The labeling instructions are an important aspect of the invention in that before a composition can be approved for any particular use, it must be approved for marketing by the United States Food and Drug Administration. Part of that process includes providing a label that will accompany the pharmaceutical composition which is ultimately sold. While the label will include a definition of the composition and such other items such as the clinical pharmacology, mechanism of action, drug resistance, pharmacokinetics, absorption, bioavailability, contraindications and the like, it will also provide the necessary dosage, administration and usage. Thus, the combination of the composition with the dropper bottle with appropriate treatment instructions is important for the proper usage of the drug once it gets on the market. Such treatment instructions will describe the usage in accordance with the method of treatment set forth herein before.

Having now generally described this invention, the same will be better understood by reference to certain specific examples which are included herein for purposes of illustration only and are not intended to be limiting of the invention or any embodiment thereof, unless so specified.

In the following examples, the viscosity is determined at room temperature (20–25° C.) using a Brookfield viscometer model DV-I+, spindle #27 at 12 revolutions per minute (rpm). If the measured viscosity is less than 4,000 cP, spindle #21 should be used instead of #27.

EXAMPLES

Example I

This example sets forth a pourable gel composition of this invention. The procedure set forth in steps a-f produces a composition according to Table I. The composition is referred to as "Clindagel." An application to designate Clindagel as a trademark has been filed.

TABLE I

| Component | % w/w |
|---|---|
| Clindamycin phosphate, USP (equivalent to 1% clindamycin) | 1.19 |
| Methylparaben | 0.15 |
| CARBOPOL ® 941 (or 981) | 0.20 |
| Propylene glycol | 15.0 |
| Polyethylene glycol 400 | 5.0 |
| Sodium hydroxide (10% solution) | QS pH 5.3 to 5.7 |
| Purified water | QSAD 100.00 |

The viscosity of this composition is about 1,000 cP.

a. Weigh approximately 90% of the purified water into a stainless steel kettle. Add the propylene glycol and polyethylene glycol 400. Stir with propeller mixer.

b. At room temperature add methylparaben to step a) with continued stirring. Mix until dissolved.

c. While continuing to mix, add clindamycin phosphate to step b). Mix until dissolved.

d. While continuing to mix, add CARBOPOL® 981 or 941 slowly to step c), avoiding clumping. Mix vigorously at room temperature until a uniform and lump-free dispersion is achieved.

e. While mixing, add sufficient sodium hydroxide, 10% solution, to achieve a pH of 5.3 to 5.7. Mix until uniform.

f. Add the remaining water to make 100% and mix until uniform.

Example II

This example shows the composition of a commercially available product containing clindamycin phosphate. The product is sold by Pharmacia as Cleocin T® Gel. The components and amounts were analyzed to be as follows:

TABLE II

| Component | % w/w |
|---|---|
| Clindamycin phosphate | 1.19 |
| Carbomer 934 P | 0.8 |
| Propylene glycol | 4.9 |
| Polyethylene glycol 400 | 10.2 |
| Sodium hydroxide | QS pH 5.4 |
| Methylparaben | 0.3 |
| Allantoin | 0.2 |
| Purified water | QSAD 100 |

The viscosity of this composition is about 20,000 cP.

Example III

Comparison of Clindagel and Cleocin-T® Gel

This example provides clinical data showing the advantages of a composition of the invention as compared to a known commercial composition.

A multi-center investigator-blind clinical trial was conducted comparing a composition of this invention (see Example I) Clindagel, once daily, and Cleocin-T® Gel (see Example II), twice daily (according to manufacturer's directions), in acne vulgaris. Three hundred and twenty four patients, half in each group, were treated for up to 12 weeks.

The investigator was "blinded" in that she/he did not know which treatment the patient used before the investigator evaluated the condition of the patient's acne.

Evaluations included inflammatory lesion count, total lesion count, physician's global assessment and skin-related side effects. Papules and pustules were considered inflammatory lesions. Total acne lesions included open and closed comedones in addition to inflammatory lesions. The physician's global severity assessment was based 15 on a nine-point scale. At study end (12 weeks or last evaluation) it was concluded that Clindagel used once a day was equal in effectiveness to Cleocin-T® used twice daily and Clindagel had significantly fewer side effects. The data on lesion counts are summarized in Table III.

TABLE III

Improvement in Acne Lesions at Endpoint: Clindagel ™ Once Daily vs. Cleocin-T Gel Twice Daily.

| ACNE LESIONS | Percent Change from Baseline (standard deviation) | | |
|---|---|---|---|
| | Clindagel ™ Once Daily | Cleocin-T ® Gel Twice Daily | 95% Confidence Lower Bound |
| Inflammatory | −50.90 (2.62) | −50.02 (2.62) | 0.897 |
| Total | −37.27 (2.44) | −39.52 (2.44) | 0.801 |

The physician's global assessment is summarized in Table IV.

TABLE IV

Summary of Number of Patients with a Two-Category Improvement from Baseline in the 9-Point Physician's Global Severity Assessment at Endpoint

| PHYSICIAN's GLOBAL Assessment | Number of Patients | | |
|---|---|---|---|
| | Clindagel ™ Once Daily | Cleocin-T ® Gel Twice Daily | 95% Confidence Lower Bound |
| Improved by 2 categories | 84 | 84 | 0.833 |
| Same or Worsened | 72 | 73 | |
| TOTAL | 156 | 157 | |

The frequency of dermal side effects from Clindagel™ once daily and from Cleocin-T® twice daily are tabulated in Table V.

TABLE V

Summary Results of Frequency of Adverse Events Comparing Clindagel ™ Once Daily and from Cleocin-T ® Twice Daily.

| Category | ADVERSE EVENTS | | |
|---|---|---|---|
| | Clindagel ™ Once Daily | Cleocin-T ® Gel Twice Daily | Fisher's Exact Test |
| Number of patients in safety evaluation | 168 | 165 | |
| Number of patients with at least one skin/appendage disorder reported | 2 | 13 | 0.003 |
| Frequency of local adverse reactions | 1.2% | 7.9% | |

Example IV

This example sets forth the results of a user preference test (with vehicles, not actives) comprising a composition of this invention is shown in Example I (with CARBOPOL® 981) with the commercially available composition of Example II, (with Carbomer 934 P). Table VI sets forth the formulation compositions.

The study was conducted amongst a normal subject patient population of 10 in order to evaluate the functional and cosmetic attributes using a half-face, paired, and symmetrical design.

TABLE VI

| Component Vehicle Formulae: | % w/w Clindagel | Cleocin-T Gel |
|---|---|---|
| Carbomer 934P | — | 0.8 |
| Carbomer 981 | 0.2 | — |
| Propylene glycol | 15.0 | 4.9 |
| Polyethylene glycol 400 | 5.0 | 10.2 |
| Sodium hydroxide | qs to pH 5.5 | qs to pH 5.4 |
| Methylparaben | 0.15 | 0.3 |
| Allantoin | — | 0.2 |
| Purified water | QSAD 100 | QSAD 100 |

Test articles (gel vehicles) were identified by blinded identification code, thereby preventing test subject from knowing the identity of the test articles being applied. Each test pair involved test articles L vs. R, which were used on the left and right sides of the face respectively. The test articles assigned to L and R codes were varied so that each test article was randomly evaluated on R and L test locations and by order of application.

The subjects were equally balanced for sex. The mean age of the population was 34 years old within an age range of 25–44 years.

The following attributes were assessed during and after application: spreadability, feel/texture during application, ease of application, ability to rub the gel into the skin, drying time on the skin, skin feel after application, overall cosmetic preference, and usability of the product. Each gel was evaluated for its functional and cosmetic attributes on a scale of 1–6, with I being Unacceptable and 6 being Excellent.

Of the nine subjects with a preference for one of the test articles, 67% preferred Clindagel vehicle over Cleocin-T vehicle. The degree of preference of Clindagel over Cleocin-T was judged "moderate" to "great" in 100% of those tested. The data are tabulated in Table VII.

TABLE VII

| | Vehicle Preference By Subject | | | | | | | | | | |
|---|---|---|---|---|---|---|---|---|---|---|---|
| Subject | 1 | 2 | 3 | 4 | 5 | 6 | 7 | 8 | 9 | 10 | TOTAL |
| Age | 26 | 39 | 44 | 42 | 25 | 28 | 42 | 35 | 33 | 26 | |
| Sex | F | F | M | M | F | F | M | F | M | M | |
| Cleocin-T | | | | | | | P | P | P | | NP 3 |
| Clindagel | P | P | P | P | P | P | | | | | NP 6 |

P = Preferred
NP = No Preference
F = Female
M = Male

There was a significantly higher score for Clindagel vehicle than for Cleocin-T gel vehicle in four of the specific attributes, and no significant difference in two of those attributes (Table VIII). Clindagel vehicle scored marks of "Very Good" in three of the six attribute categories and marks of "Good" in three other. Cleocin-T gel vehicle scored marks of "Very Good" in one category, "Good" in four categories and "Fair" in one category.

TABLE VIII

Frequency of Higher Score of Clindagel Vehicle and Cleocin-T Gel Vehicle

| Functional and Cosmetic Attribute: | Frequency of Higher Score (%) CLINDAGEL | CLEOCIN-T | No Preference |
|---|---|---|---|
| Spreadability | 30% | 30% | 40% |
| Feel/texture during application | 50% | 30% | 20% |
| Ease of application | 20% | 30% | 50% |
| Ability to rub gel into skin | 50% | 20% | 30% |
| Length of drying time | 70% | 20% | 10% |
| Skin feel after application | 50% | 30% | 20% |

Forty percent of test subjects commented independently that the Clindagel vehicle was "runny" or "watery" upon application. This was also reflected in the "Ease of Application" attribute, where Cleocin-T had a slightly higher score. 50% of test subjects commented independently on their face feeling "sticky" after application of the Cleocin-T vehicle. 80% of test subjects indicated that they would use the Clindagel vehicle as a facial medication product. Only 30% of those tested indicated that they would use Cleocin-T vehicle as a facial medication product.

Example V

Stability Study of Clindagel™ with Clindaymycin Phosphate as Active Ingredient

This example provides laboratory data showing stability of Clindagel (Example I) for at least 18 months at 25° C. Clindagel was tested for the stability of the active ingredient, clindamycin phosphate, over time at controlled room temperature (i.e., 25° C. and 60% relative humidity). A stability-indicating, high performance liquid chromatography assay was used to assess remaining clindamycin phosphate potency, expressed as clynamycin, during the experiment. Based on the data shown in Table IX, Clindagel is projected to have a commercial shelf life of about 24 months.

The estimated shelf life was calculated from the 95% confidence interval around the least squares fit to the available data. The projected shelf life is the time at which the drug potency reaches 90% of label claim (as allowed by the USP). The software used for the statistical analysis is named "SLIMStat+" and is sold by Metrics, Inc., P.O. Box 4035, Greenville, N.C. 27836, phone 252-752-3800.

TABLE IX

Room Temperature Stability Assessment of Clindamycin Potency in Clindagel ™, 1%.

| | Percent Clindamycin by Weight | | | | | |
|---|---|---|---|---|---|---|
| | Initial | 1 month | 2 months | 6 months | 12 months | 18 months |
| Clindamycin Phosphate Assay | 1.028 | 1.017 | 1.009 | 1.004 | 0.983 | 0.959 |

Example VI

Clindamycin Phosphate-Tretinoin Combination Composition

Section I

This section of this example describes two gel compositions of the invention in which the active ingredients are clindamycin phosphate and tretinoin.

Two pourable gel compositions containing a combination of clindamycin phosphate and tretinoin were made according to the invention. In Formulation A, the gel had a pH of about 5.5 and a viscosity of about 6100 cP. In Formulation B, the gel exhibited a pH of about 4.7 and a viscosity of about 6,000 cP. See quantitative formulae in Table X. This example illustrates the utility of our invention in the preparation of physically and chemically stable gel formulations.

TABLE X

Quantitative compositions of two combination Clindamycin Phosphate/Tretinoin gel formulations:

| Component | A % w/w | B % w/w |
|---|---|---|
| Tretinoin | 0.025 | 0.025 |
| Clindamycin Phosphate | 1.21 | 1.21 |
| Propyl Gallate | — | 0.02 |
| BHA | 0.02 | — |
| Citric Acid | — | 0.05 |
| Disodium Edetate | 0.05 | 0.05 |
| Polysorbate 80 | 5.0 | 0.08 |
| Propylene Glycol | 5.0 | — |
| PEG 400 | 20.0 | — |
| Glycerin | — | 10.0 |
| Methylparaben | 0.1 | 0.15 |
| CARBOPOL 981 | 0.5 | 0.5 |
| Tromethamine (10% in water) | QS to pH 5.5 | QS to pH 4.5 |
| Purified Water | QSAD 100 | QSAD 100 |

Method of preparation: Formula A a. Combine the propylene glycol, polyethylene glycol 400, and polysorbate 80. Add the tretinoin and stir to dissolve.

b. In a separate container dissolve the disodium edetate, methylparaben, and butylated hydroxyanisole in the purified water.

c. Add the clindamycin phosphate to the aqueous solution of step b and stir to dissolve.

d. Disperse the CARBOPOL 981 into the aqueous solution with high-speed stirring.

e. Add the tretinoin drug phase to the aqueous CARBOPOL dispersion with stirring and then add the tromethamine and mix to form a homogeneous gel.

Method of preparation of Formula B a. Combine the glycerin and polysorbate 80. Add the tretinoin and stir to wet and disperse.

b. In a separate container dissolve the propyl gallate, citric acid, disodium edetate, methylparaben, and butylated hydroxyanisole in the purified water.

c. Add the clindamycin phosphate to the aqueous solution of step b and stir to dissolve.

d. Disperse the CARBOPOL 981 into the aqueous solution with high-speed stirring.

e. Add the tretinoin drug phase to the aqueous CARBOPOL dispersion with stirring and then add the tromethamine and mix to form a homogeneous gel.

Section 2

This Section of this example describes two additional compositions that are slight modifications of Formulas A and B, wherein the preservatives have been changed or adjusted. The formulas are given below. C is similar to A, and D is similar to B.

TABLE XI

| Component | C % w/w | D % w/w |
|---|---|---|
| Clindamycin Phosphate | 1.24 | 1.24 |
| Tretinoin | 0.025 | 0.025 |
| Propyl Gallate | — | 0.02 |
| BHA | 0.02 | — |
| Citric Acid | — | 0.05 |
| Disodium Edetate | 0.05 | 0.05 |
| Methylparaben | — | 0.15 |
| Propylparaben | — | 0.03 |
| Benzyl Alcohol | 1 | — |
| Polysorbate 80 | 5 | 0.08 |
| Propylene Glycol | 5 | — |
| PEG 400 | 20 | — |
| Glycerin | — | 10 |
| Tromethamine (10%) | qs to pH 5.5 | qs to pH 4.5 |
| CARBOPOL 981 | 0.5 | 0.5 |
| Purified Water | qsad 100 | qsad 100 |

In making formula C, the 0.1% methylparaben preservative in Formula A was replaced with 1.0% benzyl alcohol. In Formula D, 0.03% propylparaben was added as an additional preservative (because the combination of methylparaben and propylparaben is sometimes a better preservative system). Methods of preparation:

Formula C is prepared similarly to Formula A, except that methylparaben would be omitted from step "b," and the benzyl alcohol would be added to step "a."

Formula D is prepared similarly to Formula B; propylparaben would be added to step "b."

The Formula C gel has a pH about 5.5 and a viscosity about 9000 cP. The Formula D gel has a pH about 4.6 and a viscosity about 4100 cP.

Example VII

Assessment of Chemical Stability of Tretinoin in Formulations A and B from Example VI.

This example provides laboratory data showing the stability of tretinoin in two compositions of the invention under accelerated test conditions.

Tretinoin is known to be relatively unstable, therefore, the chemical stability of these combination formulations was assessed in a 12-week accelerated stability study. The gels were packaged in amber glass vials, 8 grams each, and stored at 40° C. High performance liquid chromatography assays were performed initially and at 2, 4, and 12 weeks using the method for tretinoin cream (USP 24, page 1684). Both compositions were found to retain their potency in this accelerated study. Table XII summarizes the chemical stability results.

TABLE XII

Accelerated Temperature (40° C.) Stability Assessment of Tretinoin Potency in Formulations A and B, Example VI.

| Tretinoin Concentration | Time in weeks | | | |
|---|---|---|---|---|
| (% w/w) | 0 | 2 | 4 | 12 |
| Formula A | 0.0210 | 0.0228 | 0.0236 | 0.0231 |
| Formula B | 0.0236 | 0.0231 | 0.0234 | 0.0234 |

Example VIII

Composition of Combination Gel Formulation

This example teaches how to modify a known commercial composition of Example II to include tretinoin.

A combination gel formulation of tretinoin 0.025%, and clindamycin 1% was made by spatulating tretinoin powder and propyl gallate (an antioxidant to retard oxidative loss of tretinoin) into Cleocin®T gel (Example II). The quantitative formula is shown in Table XIII.

TABLE XIII

| Component | Amount |
|---|---|
| Tretinoin | 0.0074 g |
| Propyl Gallate | 0.0145 g |
| Cleocin ® T gel | 28.0000 g |
| TOTAL | 28.0219 g |

The tretinoin and propyl gallate were accurately weighed, placed on a glass plate, and incorporated into the Cleocin®T gel with a spatula. During spatulation, the product was protected from light. The resulting product was a smooth, clear light yellow gel with a pH of 5.7 and a viscosity of about 20,000 cP.

Example IX

Physical Stability Studies of the Compositions of Example VI (Formula A) and Example VIII This example compares a composition of the invention (Example VI, Formula A) with a modified commercial composition (Example VIII) with regards to crystal growth.

The physical stability of Example VI, Formula A and Example VIII, was assessed over a 4-week period at 5° C., 40° C. and 50° C. The stability evaluation was based on careful physical examination for description at initial, 2 week and 4 week times. At study end, microscopic examination was performed to check for precipitation of tretinoin and crystal growth. As illustrated in the data summary below (Table XIV), the modified commercial formulation, Cleocino®T gel, was physically unstable compared to a composition of the invention, Example VI (Formula A).

TABLE XIV

Description: Clear Light Yellow Gel

| | Initial | 2 weeks | 4 weeks |
|---|---|---|---|
| Example VI (Formula A) | | | |
| 5° C. | Clear | Clear | Clear - no crystals |
| 40° C. | Clear | Clear | Clear - no crystals |
| 50° C. | Clear | Clear | Clear - no crystals |
| Example VIII | | | |
| 5° C. | Clear | Hazy | Hazy - Crystals to 1200 microns |
| 40° C. | Clear | Translucent | Hazy - Crystals to 1200 microns |
| 50° C. | Clear | Translucent | Hazy - Crystals to 1200 microns |

Example X

This example sets forth a lotion composition of this invention comprising two active ingredients: an antibiotic, i.e., clindamycin phosphate, and a retinoid, i.e., tretinoin. The components for this lotion are set forth in Table XIV.

TABLE XIV

| Component | % w/w |
| --- | --- |
| Clindamycin Phosphate | 1.21 |
| Tretinoin | 0.025 |
| Stearyl Alcohol | 5.00 |
| Diisopropyl Adipate | 6.00 |
| PEG 40 Stearate (Myrj 52) | 2.00 |
| Sorbitan Stearate (Span 60) | 2.00 |
| Butylated Hydroxytoluene | 0.02 |
| Propylene Glycol | 5.00 |
| Methylparaben | 0.15 |
| Propylparaben | 0.03 |
| Citric Acid | 0.05 |
| Disodium Edetate | 0.10 |
| CARBOPOL 981 | 0.10 |
| Tromethamine (10%) | qs pH 5.5 |
| Purified Water | qsad 100 |

The viscosity of this composition is about 7,000 cP.
Method of preparation:
a. Combine the propylene glycol and purified water. Add the methylparaben, propylparaben, citric acid, and disodium edetate and stir to dissolve.
b. Add the clindamycin phosphate to step "a" and stir to dissolve.
c. Add the Carpobol 981 to step "b" and stir to form a homogeneous dispersion.
d. Warm step "c" water phase to between 60° C. and 70° C.
e. Combine the stearyl alcohol. PEG 40 stearate, sorbitan stearate, and butylated hydroxytoluene and warm to melt at between 60° C. to 70° C.
f. Add the tretinoin to the diisopropyl adipate and stir to dissolve.
g. With high-speed stirring add step "e" oil phase and step "f" drug phase sequentially to step "d" water phase and mix well.
h. Cool emulsion with continued stirring.
i. Add the tromethamine solution and stir to form a homogeneous emulsion. Cool to room temperature with continued stirring.

Example XI

This example sets forth a pourable gel composition of this invention which gel contains a corticosteroid. Such formulation is suitable for treating inflammatory skin conditions such as atopic dermatitis.

| Component | % by weight |
| --- | --- |
| Halobetasol propionate, micronized | 0.05 |
| Docusate sodium | 0.10 |
| CARBOPOL ® 981 | 0.3 |
| Propylene glycol | 12 |
| Methylparaben | 0.1 |
| Propylparaben | 0.02 |
| Tromethamine | QS pH 6.5 |
| Purified water | QSAD 100.00 |

The viscosity of this composition is about 6200 cP.
a. Dissolve the methylparaben and propylparaben in the propylene glycol at room temperature using a propeller mixer.
b. Weigh 70% of the formula weight of purified water and slowly add the solution from step "a" while mixing with propeller mixer.
c. While continuing to mix, add CARBOPOL® 981 slowly to step "b." Mix at room temperature until a smooth and uniform dispersion is produced.
d. To 10% of the formula weight of water add the docusate sodium and mix until fully dissolved. To facilitate dissolution the mixture may be warmed to 40–50° C., and then cooled to room temperature when dissolution is complete.
e. Disperse the micronized halobetasol propionate in step "d" with a propeller mixer or preferably a homogenizer of the rotor-stator type.
f. Add step "e" to step "c" using propeller mixer to uniformly disperse the drug material.
g. Dissolve the tromethamine in 10 times its weight in purified water. While mixing, use the tromethamine solution to adjust the pH and thicken the gel. Continue incremental additions until a pH of about 6.5 is attained.
h. Add water to make 100% of the batch size and mix until homogeneous with a propeller-type mixer.

Example XII

This example sets forth yet another pourable gel composition of this invention. The formulation contains metronidazole for topical application to the skin areas affected, for example, with rosacea.

| Component | % by weight |
| --- | --- |
| Metronidazole | 0.75 |
| Methylparaben | 0.12 |
| Propylparaben | 0.03 |
| CARBOPOL ® 981 | 0.25 |
| Glycerin | 5.00 |
| Trolamine | QS pH 8 |
| Purified Water | QSAD 100 |

The viscosity of this composition is about 4700 cP.
a. Weigh 90% of the formula weight of purified water, metronidazole, glycerin, methyl-paraben and propylparaben into a suitable stainless steel container. Mix vigorously at room temperature until all components are dissolved. A propeller-type mixer is particularly suitable.
b. While continuing to mix, slowly add the CARBOPOL®. Mix until a lump-free dispersion is attained.
c. Mix the trolamine with an equal part of purified water. Use this solution to adjust the pH to about 8 with incremental additions while mixing.
d. Add the balance of the purified water to make 100% and mix until a homogeneous gel is produced.

Example XIII

This example sets forth a pourable gel composition of this invention which gel contains a NSAID agent.

| Component | % by weight |
| --- | --- |
| Naproxen | 1.00 |
| Octoxynol 9 | 0.10 |
| CARBOPOL ® 981 | 0.30 |
| Propylene glycol | 5.00 |

-continued

| Component | % by weight |
| --- | --- |
| Glycerin | 5.00 |
| Benzyl alcohol | 1.00 |
| Sodium hydroxide, 10% solution | QS pH 3.0 to 3.5 |
| Purified water | QSAD 100.00 |

The viscosity of this composition is about 4200 cP.

a. Mix the benzyl alcohol, glycerin and propylene glycol together at room temperature using a propeller mixer.

b. Weigh 70% of the formula weight of purified water and slowly add the solution from step "a" while mixing with propeller mixer.

c. While continuing to mix, add CARBOPOL® 981 slowly to step "b." Mix at room temperature until a smooth and uniform dispersion is produced.

d. To 2–5% of the formula weight of water add the octoxynol 9 and mix until fully dissolved.

e. Disperse the naproxen in step "d" with a propeller mixer or a homogenizer.

f. Add step "e" to step "c" using propeller mixer to uniformly disperse the drug material.

g. While mixing, use the sodium hydroxide solution to adjust the pH. Continue incremental additions until a pH of 3.0 to 3.5 is attained.

g. Add water to make 100% of the batch size and mix until homogeneous with a propeller-type mixer.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

The subject matter claimed is:

1. A composition having a pH of about 3 to about 9 and a viscosity of less than about 15,000 cP for treating a skin disorder in a human subject, which composition consists essentially of
    (a) a therapeutically-effective amount of at least one compound useful for treating such disorder,
    (b) a pharmaceutically-acceptable, lightly cross-linked hydrophilic, polyacrylic acid polymer compatible with the compound,
    (c) a pharmaceutically-acceptable base to adjust pH,
    (d) up to about 25% w/w of at least one water miscible solvent,
    (e) optionally a preservative,
    (f) water, and
    (g) at least one surfactant in combination with an oil phase sufficient to form a lotion.

2. The composition of claim 1, wherein the compound is an antibiotic, imidazole, retinoid, corticosteroid, or a non-steroidal anti-inflammatory drug (NSAID).

3. The composition of claim 2, wherein the compound is an antibiotic alone or in combination with a corticosteroid or a retinoid.

4. The composition of claim 3, wherein the compound is an antibiotic alone.

5. The composition of claim 3, wherein an antibiotic is combined with a corticosteroid, the antibiotic is clindamycin phosphate, and the corticosteroid is desonide, hydrocortisone valerate, fluocinolone acetonide, hydrocortisone butyrate, or triamcinolone acetonide.

6. The composition of claim 3, wherein an antibiotic is combined with a retinoid, the antibiotic is clindamycin phosphate, and the retinoid is tretinoin.

7. The composition of claim 6 having a pH of about 5 to 6, which composition is a lotion consisting essentially of
    (a) (i) about 0.5% to about 2.0% w/w clindamycin phosphate and (ii) about 0.01% to about 0.05% w/w tretinoin,
    (b) about 0.1% to about 0.5% w/w of the polymer,
    (c) the base to adjust pH,
    (d) the water-miscible solvent,
    (e) less than about 0.2% of a preservative,
    (f) water, and
    (g) an oil phase in combination with at least one surfactant to form an emulsion.

8. The composition of claim 2, having a corticosteroid as the sole active agent.

9. The composition of claim 8, wherein the corticosteroid is diflorasone diacetate, fluticasone propionate, halobetasol propionate, budesonide, desonide, betamethasone dipropionate, clobetasol propionate, hydrocortisone butyrate, betamethasone valerate, or fluocinolone acetonide, or triamcinolone acetonide.

10. The composition of claim 1 in combination with a container that accurately administers a portion of the composition for topical administration to a patient.

11. The composition of claim 10 in combination with labeling instructions for use in treating the skin disorder.

12. A method for treating a skin disorder in a human subject, which method comprises topically administering a composition having a pH of about 3 to about 9 and a viscosity of less than about 15,000 cP to an affected area of the subject's skin having such disorder in an amount and for a period of time sufficient to improve the skin disorder, wherein the composition consists essentially of
    (a) a therapeutically-effective amount of at least one compound useful for treating such disorder,
    (b) a pharmaceutically-acceptable lightly cross-linked hydrophilic polyacrylic acid polymer compatible with the pharmaceutical active material,
    (c) a pharmaceutically-acceptable base to adjust pH,
    (d) up to about 25% w/w of at least one water miscible solvent,
    (e) optionally a preservative,
    (f) water, and
    (g) an oil phase in combination with a surfactant sufficient to form a lotion.

13. The method of claim 12, wherein the skin disorder is an inflammatory skin disorder, acne, or rosacea.

14. The method of claim 13, wherein the composition is administered once a day for the period of time sufficient to improve the skin disorder.

15. The method of claim 14, wherein the compound of the composition is an antibiotic, imidazole, retinoid, corticosteroid, or NSAID.

16. The method of claim 15, wherein the compound is an antibiotic alone or in combination with a corticosteroid, or a retinoid.

17. The method of claim 16, wherein the compound is an antibiotic in combination with a corticosteroid.

18. The method of claim 16, wherein the antibiotic is clindamycin phosphate and is combined with the retinoid tretinoin.

19. The method of claim 18, wherein the composition is a lotion having a pH of about 5 to 6, consisting essentially of
(a) (i) about 0.5% to about 2.0% w/w clyndanycin phosphate and (ii) about 0.01% to about 0.05% w/w tretinoin,
(b) about 0. 1% to about 0.5% w/w% of the polymer,
(c) the base to adjust pH,
(d) the water-miscible solvent,
(e) less than about 0.2% of a preservative,
(f) water, and
(g) an oil phase in combination with at least one surfactant to form an emulsion.

20. The method of claim 15, wherein composition contains a corticosteroid as the sole active agent.

21. The method of claim 20, wherein the corticosteroid is diflorasone diacetate, fluticasone propionate, halobetasol propionate, budesonide, desonide, betamethasone dipropionate, clobetasol propionate, hydrocortisone butyrate, betamethasone valerate, fluocinolone acetonide, or triamcinolone acetonide.

22. A method of preparing a composition having a viscosity of less than about 15,000 cP and a pH of about 3 to 9 useful for treating a skin disorder in a human subject, which method comprises
(a) combining water and optionally a water miscible solvent with a therapeutically-effective amount of at least one compound useful for treating such disorder and a pharmaceutically-acceptable, lightly cross-linked hydrophilic polyacrylic acid polymer compatible with the compound,
(b) adjusting the pH to about 3 to 9, and
(c) optionally combining a preservative, a water-miscible solvent (if not included before) and at least one surfactant in combination with an oil phase component to form a lotion.

23. The method of claim 22, wherein the compound is an antibiotic, imidazole, retinoid, corticosteroid, or a NSAID.

24. The method of claim 23, wherein the compound is an antibiotic alone or in combination with a corticosteroid or a retinoid.

25. The method of claim 23, wherein the antibiotic is combined with a corticosteroid, the antibiotic is clindamycin phosphate, and the corticosteroid is desonide, hydrocortisone valerate, fluocinolone acetonide, hydrocortisone butyrate, or triamcinolone acetonide.

26. The method of claim 23, wherein the antibiotic is combined with a retinoid, the antibiotic is clindamycin phosphate, and the retinoid is tretinoin.

27. The method of claim 26, wherein the composition is a lotion having a pH of about 5 to 6 and consists essentially of
(a) (i) about 0.5% to about 2.0% w/w clindamycin phosphate and (ii) about 0.010/% to about 0.05% w/w tretinoin,
(b) about 0.1% to about 0.5% w/w of the polymer,
(c) the base to adjust pH,
(d) the water-miscible solvent,
(e) less than about 0.2% of a preservative,
(f) water, and
(g) an oil phase in combination with at least one surfactant to form an emulsion.

28. The method of claim 23, wherein the composition has a corticosteroid as the sole active agent.

29. The method of claim 28, wherein the corticosteroid is diflorasone diacetate, fluticasone propionate, halobetasol propionate, budesonide, desonide betamethasone dipropionate, clobetasol propionate, hydrocortisone butyrate, betamethasone valerate, fluocinolone acetonide, or triamcinolone acetonide.

30. The method of claim 22, which method further comprises placing the composition in a container from which drops are accurately administered for topical administration to a patient.

31. The method of claim 30, which method further comprises combining the container with labeling instructions for use in treating the skin disorder.

* * * * *